US011925755B2

(12) United States Patent
Gerlach (10) Patent No.: US 11,925,755 B2
(45) Date of Patent: Mar. 12, 2024

(54) IMPELLER WITH REDUCED MASS INERTIA FOR A RESPIRATION THERAPY APPLIANCE

(71) Applicant: Loewenstein Medical Technology S.A., Luxembourg (LU)

(72) Inventor: Angela Gerlach, Hamburg (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 203 days.

(21) Appl. No.: 17/113,381

(22) Filed: Dec. 7, 2020

(65) Prior Publication Data
US 2021/0170125 A1 Jun. 10, 2021

(30) Foreign Application Priority Data
Dec. 9, 2019 (DE) .......................... 102019008521.3

(51) Int. Cl.
*A61M 16/00* (2006.01)
*F04D 29/26* (2006.01)
*A61M 16/06* (2006.01)

(52) U.S. Cl.
CPC ......... *A61M 16/0066* (2013.01); *F04D 29/26* (2013.01); *A61M 16/06* (2013.01)

(58) Field of Classification Search
CPC .............. A61M 16/0066; A61M 16/06; A61M 16/0057; F04D 29/26; F04D 29/30; F04D 29/281; F04D 29/28; F04D 29/282; F05D 2240/304

USPC ......................................................... 416/181
See application file for complete search history.

(56) References Cited

U.S. PATENT DOCUMENTS

| 5,573,369 | A  | * | 11/1996 | Du ........................... A47L 5/22 415/206 |
| 9,004,067 | B2 | * | 4/2015  | Kenyon ............ A61M 16/0057 415/206 |
| 2004/0219013 | A1 | * | 11/2004 | Hopfensperger ... F04D 29/4233 415/206 |
| 2004/0240999 | A1 | * | 12/2004 | Kamoshita ............ F04D 29/281 416/179 |
| 2005/0186077 | A1 |   | 8/2005  | Lee et al. |
| 2007/0065279 | A1 |   | 3/2007  | Lin et al. |
| 2008/0178879 | A1 |   | 7/2008  | Roberts et al. |
| 2019/0055957 | A1 | * | 2/2019  | Nakatani ................. F04D 17/16 |
| 2019/0269871 | A1 | * | 9/2019  | Shrubb ............... A61M 16/024 |

FOREIGN PATENT DOCUMENTS

EP  0627560 A1 * 12/1994 ........... F04D 29/281
EP  0627560 A1    12/1994

* cited by examiner

*Primary Examiner* — Juan G Flores
*Assistant Examiner* — Eric A Lange
(74) *Attorney, Agent, or Firm* — Abel Schillinger, LLP (57) ABSTRACT

A respiration therapy appliance having a fan for generating a respiratory air flow for carrying out respiration therapy. The fan comprises at least one rotatable fan impeller having a plurality of blade elements which are arranged on a support disk. The blade elements and/or the support disk have at least one cutout.

20 Claims, 9 Drawing Sheets

IMPELLER WITH REDUCED MASS INERTIA FOR A RESPIRATION THERAPY APPLIANCE

CROSS-REFERENCE TO RELATED APPLICATIONS

The present application claims priority under 35 U.S.C. § 119 of German Patent Application No. 102019008521.3, filed Dec. 12, 2019, the entire disclosure of which is expressly incorporated by reference herein.

BACKGROUND OF THE INVENTION

Field of the Invention

The present invention relates to a respiration therapy appliance having at least one fan for generating a respiratory air flow for carrying out respiration therapy. The fan comprises at least one rotatable fan impeller with a plurality of blade elements.

Discussion of Background Information

Appliances of the type mentioned above are used, for example, for ventilation or respiratory assistance or for cough assistance. To ensure that the treatment or therapy does not cause annoyance, the fan should make as little noise as possible during operation. For targeted respiration therapy, it is also important that adjustments to the speed of rotation of the fan impeller can take place as smoothly and as quickly as possible.

In view of the foregoing, it would be advantageous to have available a respiration therapy appliance that is able to advantageously meet the aforementioned requirements.

SUMMARY OF THE INVENTION

The present invention provides a respiration therapy appliance as well as a fan impeller as set forth in the independent claims. Developments and advantageous embodiments are set forth in the dependent claims. Further advantages and features will become clear from the general description and from the description of the illustrative embodiments.

The respiration therapy appliance according to the invention comprises at least one fan for generating a respiratory air flow. The fan comprises at least one rotatable fan impeller. The fan impeller comprises a plurality of blade elements on a support disk, and at least one cutout.

The present invention provides in particular a respiration therapy appliance 1 having at least one fan 2 for generating a respiratory air flow for carrying out respiration therapy, the fan 2 having at least one rotatable fan impeller 3 with a hub 33, which is located at the center point 32 of the fan impeller, with a support disk 16 which extends in a radial direction starting from the hub, the support disk having an outer radius 19 which defines a circumference 18, with a plurality of blade elements 4 which are arranged with their base 15 on the support disk 16 and starting from the hub extend in a radial direction to their blade tip 22 and starting from the base 15 on the cover disk extend in an axial direction and there define a longitudinal side 14, the blade elements 4 having at least one outer radius 21 at the blade tips 22, which defines the outer circumference 20 of the blade elements 4, wherein the blade elements 4 and/or the support disk 16 have at least one cutout 17.

In a preferred embodiment, the present invention further provides that the cutout 17 is formed in the material of the fan impeller 3.

In a preferred embodiment, the present invention further provides that a plurality of cutouts 17 are formed next to one another in the circumferential direction of the fan impeller 3.

In a preferred embodiment, the present invention further provides that a plurality of cutouts 17 are formed behind one another in the radial direction of the fan impeller 3.

In a preferred embodiment, the present invention further provides that the cutout 17 is formed in the support disk 16.

In a preferred embodiment, the present invention further provides that at least one through-hole 17 is formed in the support disk 16 between two blade elements 4.

In a preferred embodiment, the present invention further provides that the blade elements 4 are arranged within a circumference 18 of the disk 6, and/or wherein the blade elements 4 do not protrude beyond the circumference of the disk 6.

In a preferred embodiment, the present invention further provides that the cutout 17 is formed in the material of the blade element 4.

In a preferred embodiment, the present invention further provides that the cutout 17 is formed at the blade tip 22, and therefore the outer radius 21 is smaller than the outer radius 19 of the support disk.

In a preferred embodiment, the present invention further provides that the circumference 18 of the support disk is greater than the circumference 20 of the blade elements.

In a preferred embodiment, the present invention further provides that the cutout 17 is formed in the outer radius 19 of the support disk, and therefore the outer radius 19 is smaller than the outer radius 21 of the blade elements.

In a preferred embodiment, the present invention further provides that the circumference 20 of the blade elements is greater than the circumference 18 of the support disk.

In a preferred embodiment, the present invention further provides that the cutout 17 is formed and arranged at the blade tip 22 in such a way that the blade tip 22 is beveled in an axial direction.

In a preferred embodiment, the present invention further provides that the axial bevel lies in a range of from 1° to 50°.

In a preferred embodiment, the present invention further provides that the axial bevel lies in a range of from 1° to 25°.

In a preferred embodiment, the present invention further provides that the axial bevel lies in a range of from 2° to 20°.

In a preferred embodiment, the present invention further provides that the axial bevel lies in a range of from 3° to 16°.

In a preferred embodiment, the present invention further provides that the axial bevel lies in a range of from 4° to 7°.

In a preferred embodiment, the present invention further provides that the cutout 17 is formed and arranged at the blade tip 22 in such a way that the blade tip 22 is curved or bent in an axial direction.

In a preferred embodiment, the present invention further provides that the cutout 17 is formed and arranged at the blade tip 22 in such a way that the blade element has at least two different outer radii 21 at the blade tip 22.

In a preferred embodiment, the present invention further provides that a smaller outer radius 21 of the blade element at the blade tip 22 is arranged at or near the base 15 of the blade element 4.

In a preferred embodiment, the present invention further provides that a smaller outer radius 21 of the blade element at the blade tip 22 is arranged at or near the longitudinal side 14 of the blade element 4.

In a preferred embodiment, the present invention further provides that a smaller outer radius 21 is arranged between the longitudinal side 14 and the base 15 of the blade element 4.

In a preferred embodiment, the present invention further provides that the fan impeller 3 is produced in one piece by injection molding.

In a preferred embodiment, the present invention further provides that the cutouts have a smaller material thickness than the disk 6 or the blade elements 4. The cutouts can also be formed as through-holes.

The present invention further provides a fan impeller for a respiration therapy appliance, comprising a plurality of blade elements 4 which are arranged on a support disk 16, wherein the blade elements 4 and/or the support disk 16 have at least one cutout 17.

The respiration therapy appliance according to the invention affords many potential advantages. Thus, the fan impeller of the invention can be considerably lighter than a fan impeller of the prior art. In this way, the fan impeller has a particularly low inertia, such that the speed of rotation of the fan impeller can be adjusted particularly smoothly and with little expenditure in terms of power.

Moreover, compared to conventional fans for respiration therapy appliances, the fan according to the invention can preferably be operated at the same pressure with lower speeds of rotation. This in turn results in considerably less operating noise, such that therapy can be performed particularly quietly. It has also been found that the invention also provides considerably improved efficacy in the generation of the respiratory air flow. The invention therefore affords considerable advantages compared to other approaches.

In an advantageous embodiment, the fan impeller can be equipped on at least one axial side, preferably on only one axial side, with at least one disk. The disk is preferably suitable and designed as a support disk for at least partially securing the blade elements. It is also possible that the disk is suitable and designed as a cover disk for at least partially covering the blade elements in terms of flow technology.

The disk can be rigidly connected to the fan impeller. It is also possible that the disk is designed separate from the fan impeller or constitutes a component part separate from the fan impeller. In particular, the support disk is rigidly connected to the fan impeller and/or the cover disk is designed separate from the fan impeller.

The disk, in particular the cover disk and/or the support disk, has in particular a radially inward suction opening and/or outflow opening. It is possible that the blade elements protrude beyond the circumference of the cover disk. The cover disk is in particular not connected to the blade elements. In particular, the cover disk does not serve to secure the blade elements.

The disk, in particular the support disk and/or the cover disk, carries the blade elements. The support disk is in particular rigidly connected to the blade elements and is preferably designed in one piece with the blade elements. In particular, the support disk has a central recess, for example as part of a hub for passage of a drive shaft. The blade elements can protrude beyond the circumference of the support disk. The disk can be of a closed configuration.

The blade elements are preferably arranged within a circumference of the disk. In particular, the blade elements do not protrude beyond the circumference of the disk. However, it is also possible that the blade elements do protrude beyond the circumference of the disk.

In a particularly advantageous embodiment, the blade elements are at least partially and preferably completely straight. This permits particularly cost-effective and economical production of the fan impeller, for example by means of an injection molding method or the like. In particular, the blade elements are flat or planar. In particular, the surfaces of the blade elements are at right angles to the main plane of the support disk. For example, so-called 90° blades are provided. It is also possible to provide 90° blades +/−15°. It is also possible and preferable that the blade elements are curved. The blade elements can have a twisted or helical configuration over their longitudinal extent. The blade elements can also be bent, without being twisted about their longitudinal axis.

In particular, the blade elements of the fan impeller are all of identical configuration. However, it is also possible that the blade elements of the fan impeller are of different configurations. In particular, the blade elements are designed electively, for example alternately, with the afore-mentioned features.

The fan impeller is preferably produced or able to be produced by at least one injection molding method. Other suitable production methods can also be provided. In particular, the blade elements and/or the disk and/or the hub are produced in this way. The fan impeller can be produced from plastic or metal or also from a composite material.

The fan impeller is in particular designed in one piece. In particular, the blade elements and the disk and in particular also the hub are produced and connected to one another in one piece. It is also possible that the fan impeller is connected in one piece to the support disk and/or cover disk. The fan impeller can also be designed in several parts.

The fan impeller according to the invention is provided for a respiration therapy appliance preferably of the kind described above. The fan impeller comprises a plurality of blade elements. The fan impeller is preferably designed in the manner described above for the respiration therapy appliance according to the invention.

The invention set forth here can in particular be used in all suitable forms of fan impellers. The fan impeller can be designed as a star impeller. The fan impeller can be propeller-like or designed as a propeller. The fan impeller can preferably be encased by at least one impeller housing. The housing has in particular at least one suction opening and at least one outflow opening. The fan impeller is in particular suitable and designed to suck air in axially and blow it out or compress it radially. Other arrangements can also be provided, for example air can be sucked in axially and blown out axially, or it can be sucked in radially and blown out radially. The fan impeller can be configured as a radial impeller or axial impeller.

The fan comprises in particular at least one drive device and for example at least one electric motor. The fan is in particular operatively connected to at least one control device and is controllable via the latter. For example, specific speeds of rotation for the fan impeller can be set. The fan comprises in particular at least one suction region and at least one output region. It is possible that the suction region and/or the output region is made available by at least one disk and/or at least one housing or the like.

BRIEF DESCRIPTION OF THE DRAWING

Further features and advantages of the invention will become clear from the following description of non-limiting illustrative embodiments of the invention, which are explained in more detail below with reference to the drawings in which.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawing making apparent to those of skill in the art how the several forms of the present invention may be embodied in practice.

Figure 1:
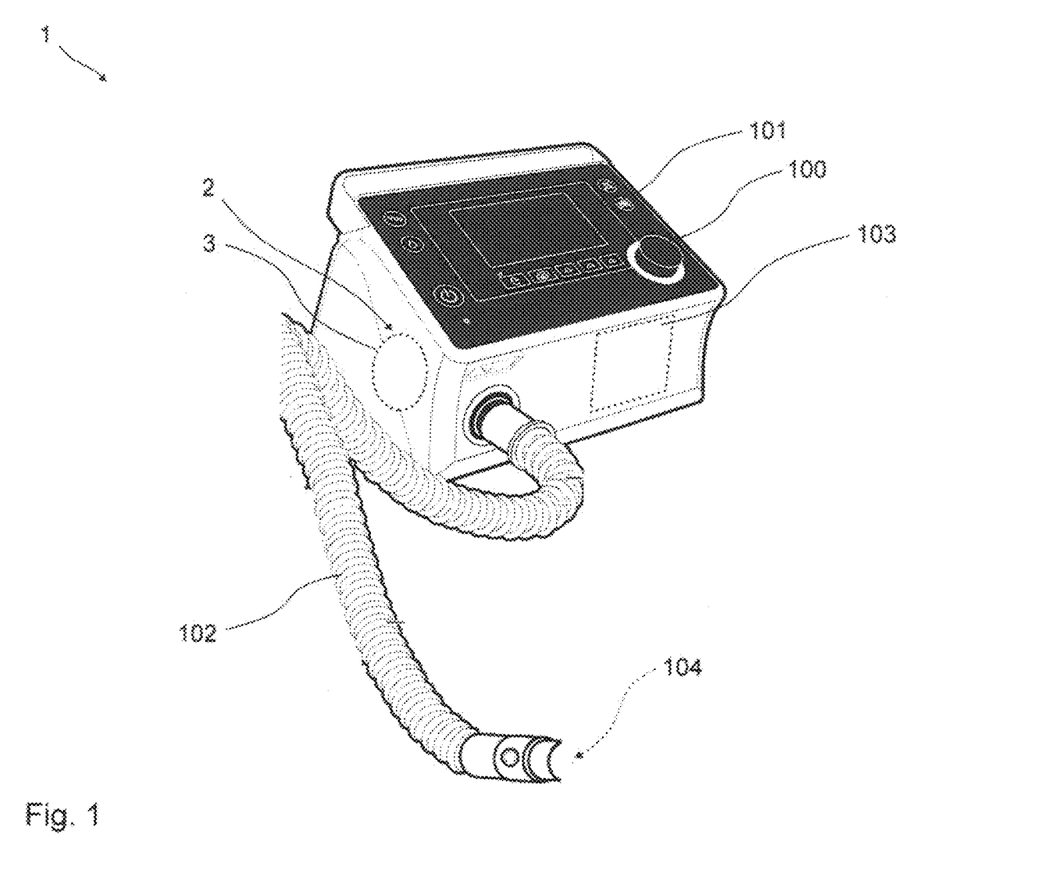
FIG. 1 shows a purely schematic perspective view of a respiration therapy appliance according to the invention.

FIG. 1 shows a respiration therapy appliance 1 according to the invention, which is a respirator for hospital use or for use at home or an emergency respirator or a respiration therapy appliance or a cough assistance appliance, for example. The appliance 1 is equipped with a fan 2 (accommodated in the appliance interior and therefore concealed here) which generates the respiratory air flow for the respiration therapy. The fan 2 is equipped with a fan impeller 3 according to the invention. The fan 2 has an electric drive for rotating the fan impeller 3.

The fan 2 is controlled by a control device 103 arranged and concealed in the appliance interior. For example, the control device 103 sets a defined speed of the fan impeller 3, according to the therapy requirements, or regulates the fan speed to a setpoint value.

The respiration therapy appliance 1 is here equipped with an operating device 100 and a display device 101. Some of the operations are performed via a touch-sensitive surface of the display device 101. The respiration therapy appliance 1 has an interface for coupling of a tube 102 for ventilation or cough assistance. The respiratory air flow generated by means of the fan 2 is delivered to the patient via the tube 102. A patient interface (not shown here) and for example a breathing mask can be attached to the tube 102.

Figure 2:
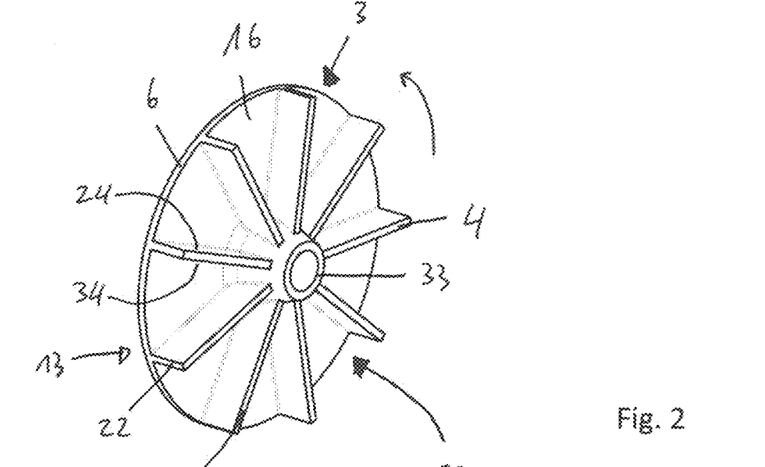
FIG. 2 shows a purely schematic perspective view of a conventional fan impeller.
Figure 3:
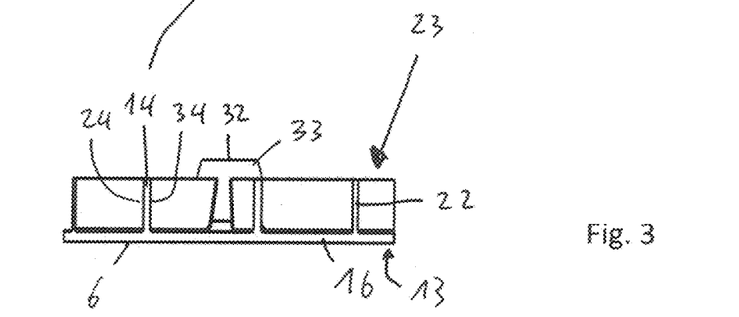
FIG. 3 shows the fan impeller from FIG. 2 in a side view.
Figure 4:
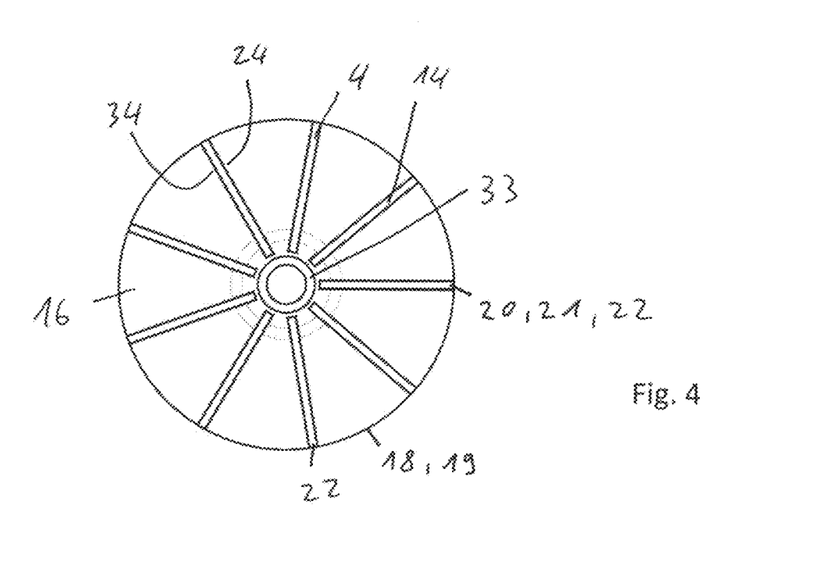
FIG. 4 shows the fan impeller from FIG. 2 in a plan view.

FIGS. 2 to 4 show a conventional fan impeller 3 in different views. The fan impeller 3 is here equipped with a plurality of blade elements 4, with a disk 6 designed as a support disk 16, and with a hub 33 for connection to a drive shaft. The blade elements 4 are here secured to the support disk 16 and preferably also to the hub 33 and are for example connected to them in one piece. The fan impeller 3 can also be designed with support disk 16 and cover disk. The blade elements 4 are then located between support disk 16 and cover disk.

The preferred direction of rotation of the fan impeller 3 is illustrated here by an arrow. The blade elements 4 have a suction side 24 and a pressure side 34. The direction of rotation of the fan impeller 3 illustrated here results in the orientation of suction side 24 and pressure side 34 illustrated here.

The fan impeller 3 shown here is, for example, integrated into the fan 2 such that air is sucked in axially and blown out radially. The suction side here lies at the axial side 23.

It will be seen from FIG. 3 and FIG. 4 that the material of the disk 6 is quite thick and that the disk is continuous. Similarly, the blade elements 4 are quite thick and/or of uniform thickness. In the embodiment shown here, the fan impeller 3 is equipped with the disk 6 only on one axial side 13. The disk 6, designed as a support disk 16, is here arranged on that axial side 13 of the fan impeller 3 that serves to receive the shaft of the motor.

Figure 5:
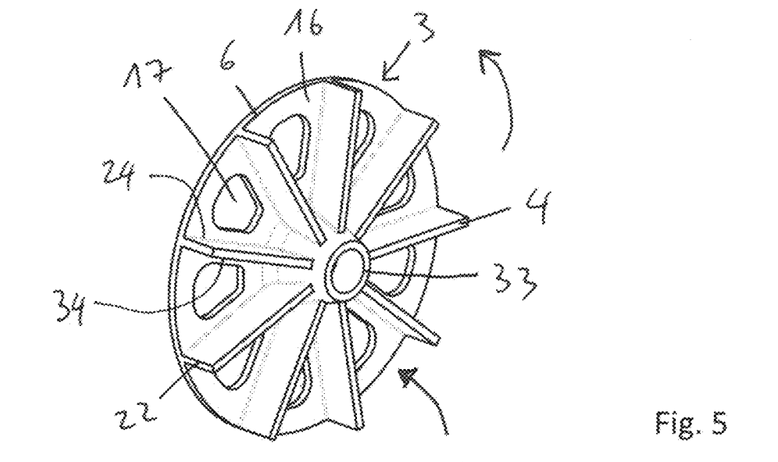
FIG. 5 shows a fan impeller according to the invention in a perspective view.
Figure 6:
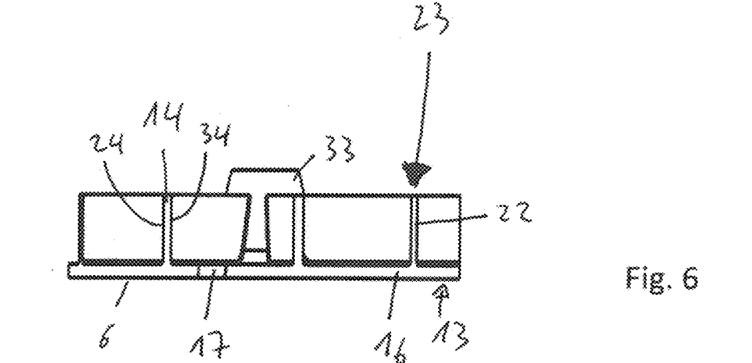
FIG. 6 shows the fan impeller from FIG. 5 in a side view.
Figure 7:
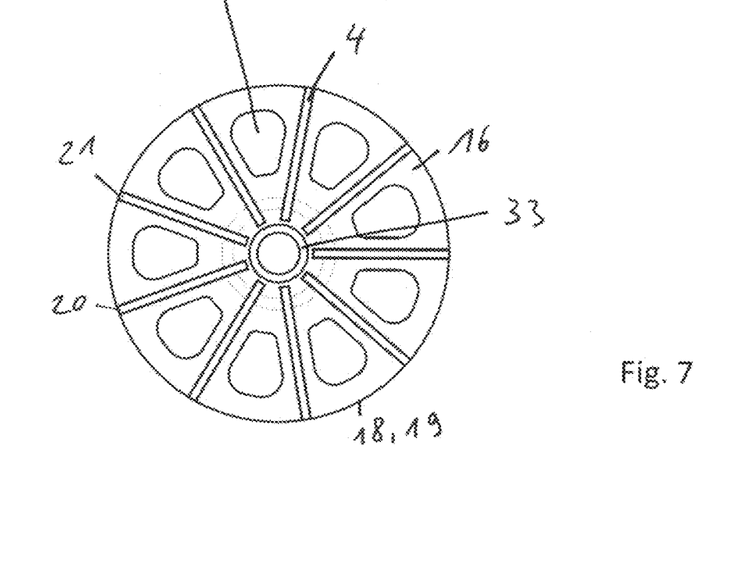
FIG. 7 shows the fan impeller from FIG. 5 in a plan view.
Figure 8:
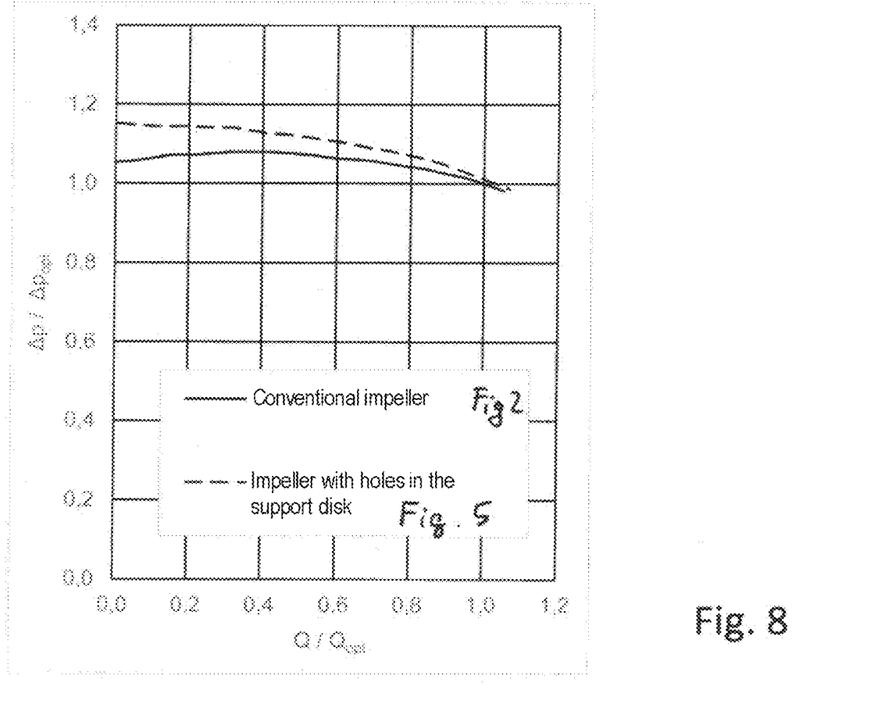
FIG. 8 shows a highly schematic graph with characteristic curves for fan impellers according to FIG. 2 and FIG. 5.

FIGS. 5 to 7 show a fan impeller 3 according to the invention which, compared to the above-described fan impeller 3, has a material cutout 17. The material cutout 17 can be designed as a thinning or hole. The fan impeller 3 has a hub 33, which is located at the center point 32 of the fan impeller, with a support disk 16 which extends in a radial direction starting from the hub, the support disk having an outer radius 19 which defines a circumference 18, with a plurality of blade elements 4 which are arranged with their base 15 on the support disk 16 and starting from the hub extend in a radial direction to their blade tip 22 and starting from the base 15 on the cover disk extend in an axial direction and there define a longitudinal side 14, the blade elements 4 having at least one outer radius 21 at the blade tips 22, which defines the outer circumference 20 of the blade elements 4. The blade elements 4 and/or the support disk 16 have at least one cutout 17. The cutout 17 is formed in the support disk 16, for example as a hole or though-hole, and between two blade elements 4. An advantage of the cutouts 17 is a greatly reduced mass moment of inertia, i.e. better acceleration and deceleration are permitted, hence improved dynamics. FIG. 8 shows two different pressure curves in diagrammatic form, in which the pressure has been plotted against the volumetric flow. The axes are standardized to an optimal operating point of the configuration of a fan impeller of the prior art without cutouts. The solid pressure curve corresponds to a fan impeller 3 according to FIGS. 2-4 without cutouts 17 (prior art). The pressure curve with the long-dashed line was found in a fan impeller 3 according to FIGS. 5-7 with cutouts 17. The characteristic curve for the fan impeller according to the invention shows even more pressure build-up. Accordingly, it can be driven at lower speed to achieve the same operating point as a customary impeller. This would give an additional reduction in noise.

Figures 9, 10:
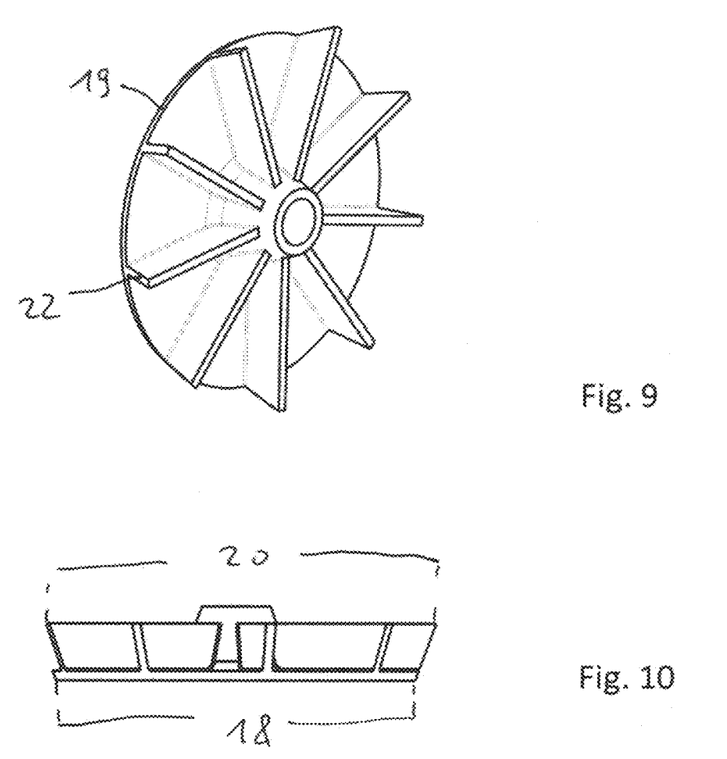
FIG. 9 shows a further fan impeller according to the invention in a perspective view.
FIG. 10 shows the fan impeller from FIG. 9 in a side view.
Figure 11:
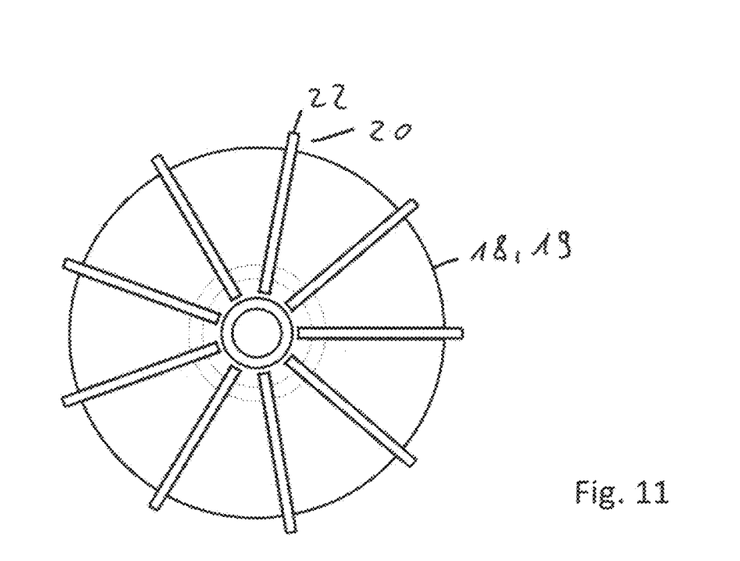
FIG. 11 shows the fan impeller from FIG. 9 in a plan view.

FIGS. 9 to 11 show a fan impeller 3 according to the invention which, compared to the fan impeller 3 as per FIG. 2, has a material cutout 17. The cutout 17 is formed in the material of the blade element 4 and at the circumference of the support disk. The cutout 17 is located at parts of the blade tip 22 and at the circumference of the support disk, and therefore the outer radius 21 is greater than the outer radius 19 of the support disk.

Accordingly, the circumference 18 of the support disk is smaller than the circumference 20 of the blade elements.

The cutout 17 is formed and arranged at the blade tip 22 in such a way that the blade tip 22 is beveled in an axial direction. The outer radius 21 at the base 15 is smaller than at the longitudinal side 14. The outer radius 21 at the base 15 can correspond to the outer radius 19 of the support disk.

The axial bevel lies in a range of from 1° to 50°. The axial bevel preferably lies in a range of from 1° to 25° or from 2° to 20°. The axial bevel also preferably lies in a range of from 3° to 16° or from 4° to 7°. According to FIGS. 9-11, the diameter changes over the axial length of the impeller, and the support disk is smaller in diameter than the blade elements.

Figure 12:
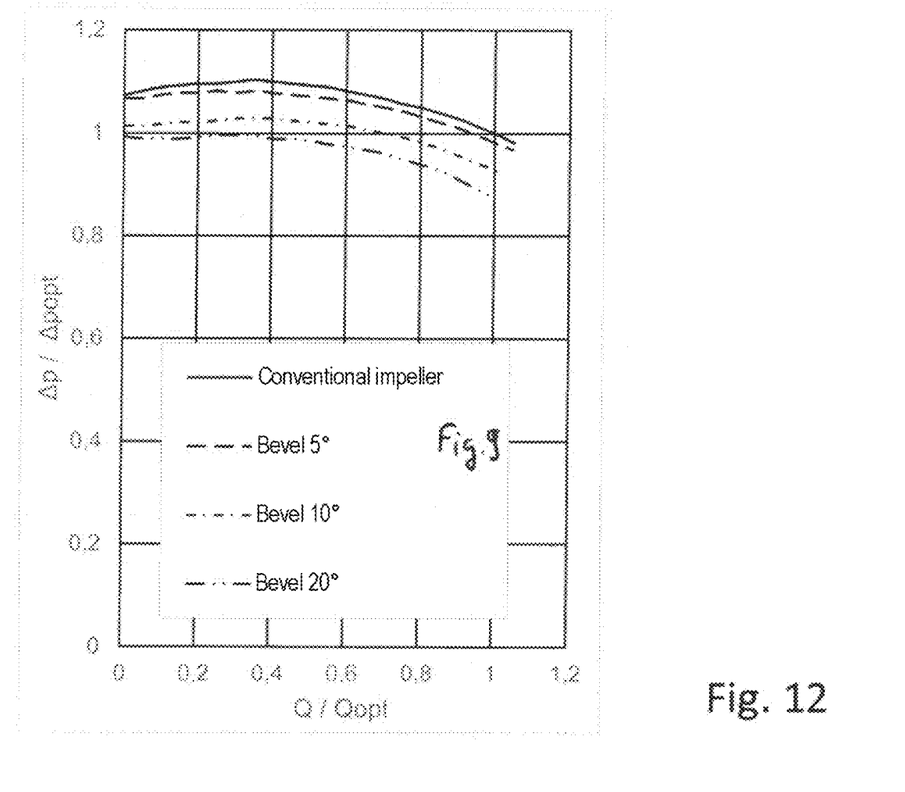
FIG. 12 shows a highly schematic graph with characteristic curves for fan impellers according to FIG. 2 and FIG. 9.

FIG. 12 shows four different pressure curves in diagrammatic form, in which the pressure has been plotted against the volumetric flow. The axes are standardized to an optimal operating point of the configuration of a fan impeller of the prior art without cutouts. The solid pressure curve corresponds to a fan impeller 3 according to FIGS. 2-4 without cutouts 17 (prior art). The pressure curve with the long-dashed line was found in a fan impeller 3 according to FIGS. 9-11 with a bevel of 5°. Compared to the impeller without bevel as per FIG. 2, there is only a slight difference in the characteristic curve relative to the pressure. This means that, with a much reduced mass moment of inertia, the characteristic curve remains practically the same. The power consumption for a beveled impeller is even lower, such that the efficacy remains the same. The characteristic curves lying below this correspond to a bevel of 10° and 20°. With a bevel of 10-15°, there is a lower characteristic curve than for an impeller without bevel as per FIG. 2. With a bevel of 20°, there is a much lower characteristic curve than for an impeller without bevel as per FIG. 2, wherein the values are still always acceptable. The pressure losses in the characteristic curve are all acceptable if the reduction in the mass moment of inertia is taken into account.

Figure 13:
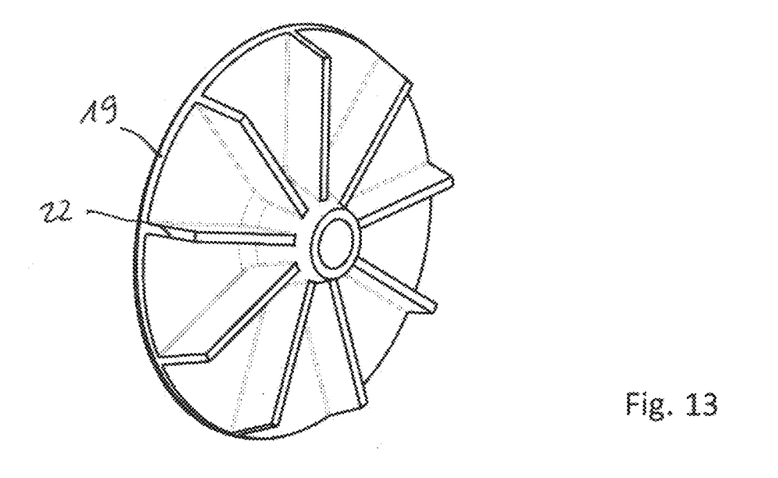
FIG. 13 shows a further fan impeller according to the invention in a perspective view.
Figure 14:
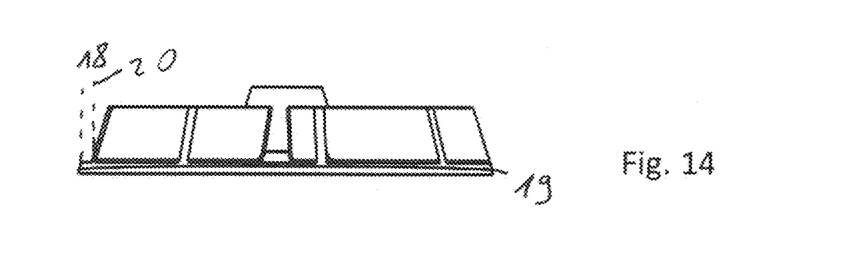
FIG. 14 shows the fan impeller from FIG. 13 in a side view.
Figure 15:
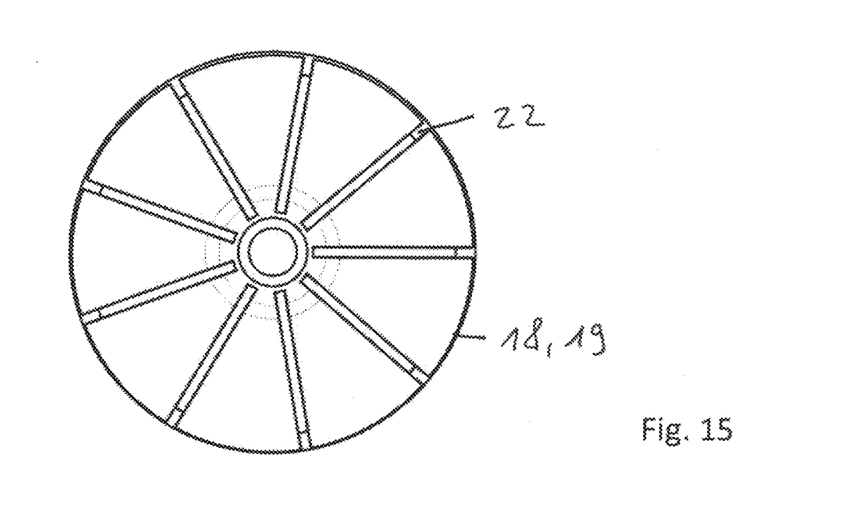
FIG. 15 shows the fan impeller from FIG. 13 in a plan view.

FIGS. 13 to 15 show a fan impeller 3 according to the invention which, compared to the fan impeller 3 as per FIG. 2, has a material cutout 17. The cutout 17 is formed in the material of the blade element 4. The cutout 17 is located at the blade tip 22, and therefore the outer radius 21 is smaller than the outer radius 19 of the support disk. Accordingly, the circumference 18 of the support disk is greater than the circumference 20 of the blade elements. The diameter changes over the axial length of the impeller. The diameter of the support disk is greater than the blade diameter.

The cutout 17 is formed and arranged at the blade tip 22 in such a way that the blade tip 22 is beveled in an axial direction. The outer radius at the base is greater than at the longitudinal side 14. The axial bevel lies in a range of between 1° and 50°. The axial bevel preferably lies in a range of between 1° and 25° or 2° and 20°.

The axial bevel also preferably lies in a range of from 3° to 16° or from 4° to 7°.

An advantage is a reduced mass moment of inertia, i.e. the impeller according to the invention is better for accelerating and decelerating. A further advantage is that the center of gravity of the impeller shifts in the direction of the support disk (and therefore the motor), which is better for the bearing.

Figure 16:
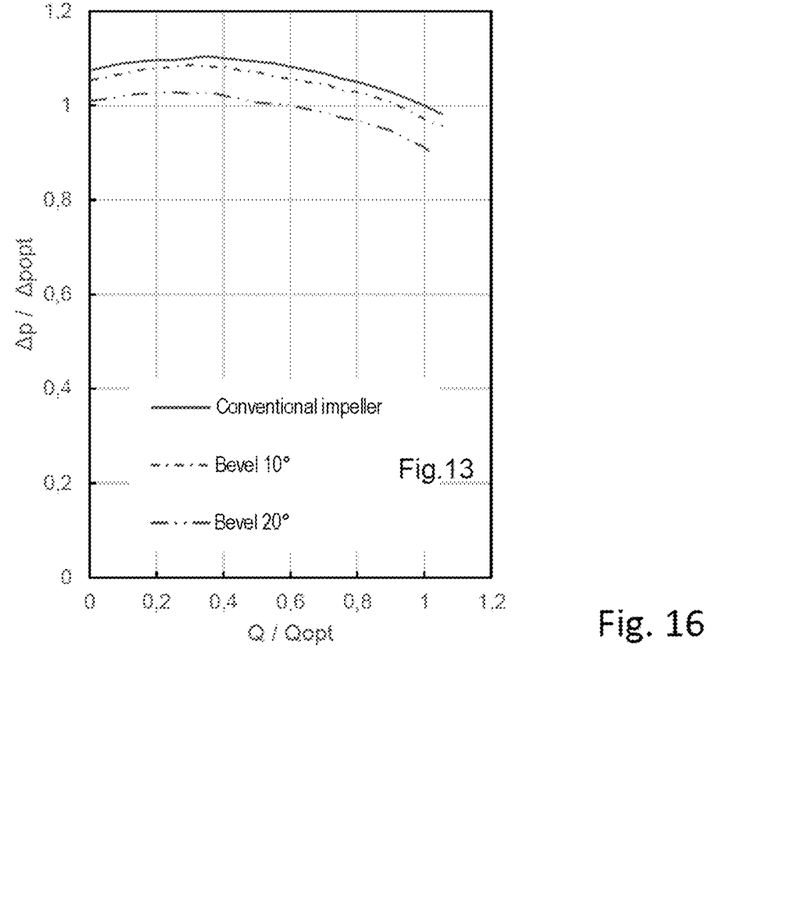
FIG. 16 shows a highly schematic graph with characteristic curves for fan impellers according to FIG. 2 and FIG. 13.
Figure 17:
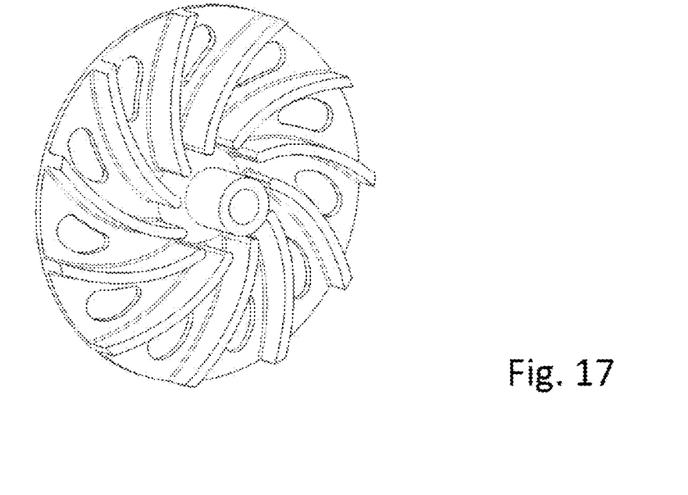
FIG. 17 shows a fan impeller analogous to that of FIG. 5, but with curved blades.
Figure 18:
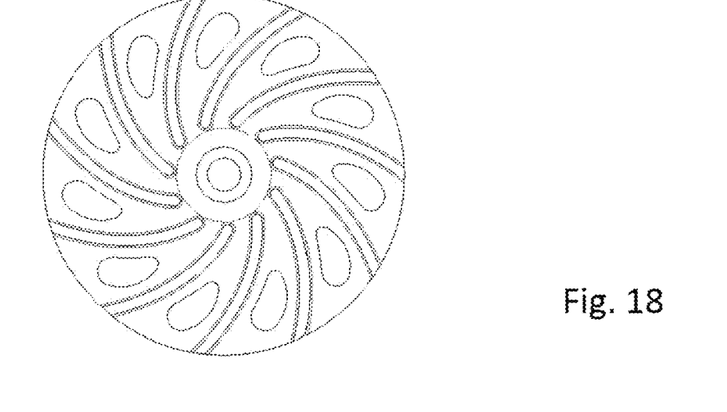
FIG. 18 shows a fan impeller analogous to that of FIG. 7, but with curved blades.
Figure 19:
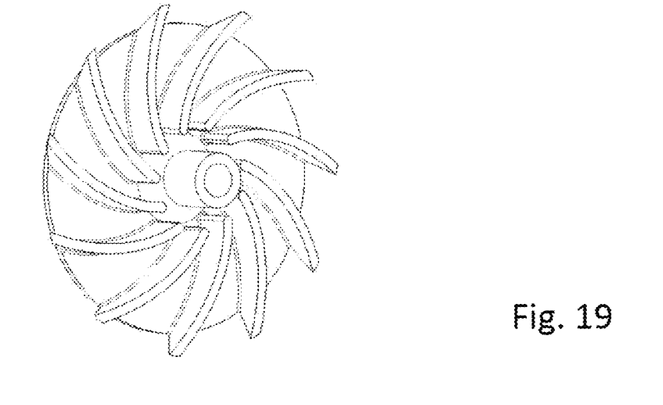
FIG. 19 shows a fan impeller analogous to that of FIG. 9, but with curved blades.
Figure 20:
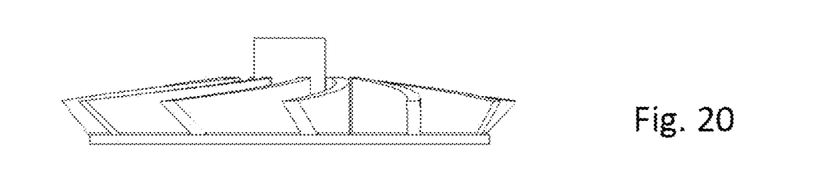
FIG. 20 shows a fan impeller analogous to that of FIG. 10, but with curved blades.

FIG. 16 shows three different pressure curves in diagrammatic form, in which the pressure has been plotted against the volumetric flow. The axes are standardized to an optimal operating point of the configuration of a fan impeller of the prior art without cutouts. The solid pressure curve corresponds to a fan impeller 3 according to FIGS. 2-4 without cutouts 17 (prior art). The pressure curve lying below was found in a fan impeller 3 according to FIGS. 13-15 with a bevel of 10°. Compared to the impeller without bevel as per FIG. 2, there is only a slight difference in the characteristic curve relative to the pressure. This means that, with a much reduced mass moment of inertia, the characteristic curve remains practically the same. The power consumption for a beveled impeller is even lower, such that the efficacy remains the same. The characteristic curves lying below this correspond to a bevel of 20°. With a bevel of 20°, there is a much lower characteristic curve than for an impeller without bevel as per FIG. 2, wherein the values are still always acceptable. The pressure losses in the characteristic curve are all acceptable if the reduction in the mass moment of inertia is taken into account. For a bevel of 5°, there was even a characteristic curve (not shown) corresponding to the characteristic curve from the prior art. The efficacy would even be increased here.

For all of the embodiments, it is also possible to use an additional disk 6 as cover disk 26. The latter then covers the blade elements 4.

The blade elements 4 are designed here as 90° blades. However, bent blades are also conceivable.

The blade elements 4 can have winglets.

The cutouts can be used in combination on the blade elements and the disks 16 and 26.

To sum up, the present invention provides:
1. A respiration therapy appliance, wherein the appliance comprises at least one fan for generating a respiratory air flow for carrying out respiration therapy, the fan comprising at least one rotatable fan impeller with a central hub, with a support disk which extends substantially in a radial direction starting from the hub, the support disk having an outer radius which defines a circumference, with a plurality of blade elements which are arranged with their base on the support disk and starting from the hub extend substantially in a radial direction to their blade tip and starting from the base on the support disk extend in an axial direction and there define a longitudinal side, the blade elements having at least one outer radius at the blade tips, the blade elements and/or the support disk comprising at least one cutout.
2. The respiration therapy appliance of item 1, wherein the blade elements, starting from the hub, extend rectilinearly to their blade tip.
3. The respiration therapy appliance of item 1, wherein the blade elements, starting from the hub, extend in a curved manner to their blade tip.
4. The respiration therapy appliance of any one of the preceding items, wherein the cutout is formed in the material of the fan impeller.

5. The respiration therapy appliance of any one of the preceding items, wherein a plurality of cutouts are formed next to one another in a circumferential direction of the fan impeller.
6. The respiration therapy appliance of any one of the preceding items, wherein a plurality of cutouts are formed behind one another in a radial direction of the fan impeller.
7. The respiration therapy appliance of any one of the preceding items, wherein the cutout is formed in the support disk.
8. The respiration therapy appliance of any one of the preceding items, wherein at least one through-hole is formed as cutout in the support disk between two blade elements.
9. The respiration therapy appliance of any one of the preceding two items, wherein the blade elements are arranged within a circumference of the disk and/or wherein the blade elements do not protrude beyond the circumference of the disk.
10. The respiration therapy appliance of any one of the preceding items, wherein the cutout is formed in a material of the blade element.
11. The respiration therapy appliance of any one of the preceding items, wherein the cutout is formed at the blade tip, and therefore the outer radius is smaller than the outer radius of the support disk.
12. The respiration therapy appliance of any one of the preceding items, wherein the circumference of the support disk is greater than the circumference of the blade elements.
13. The respiration therapy appliance of any one of the preceding items, wherein the cutout is formed in a region of the outer radius of the support disk, and therefore the outer radius of the support disk is smaller than the outer radius of the blade elements.
14. The respiration therapy appliance of any one of the preceding items, wherein the circumference of the blade elements is greater than the circumference of the support disk.
15. The respiration therapy appliance of any one of the preceding items, wherein the cutout is formed and arranged at the blade tip in such a way that the blade tip is beveled in an axial direction.
16. The respiration therapy appliance of any one of the preceding items, wherein the axial bevel ranges from 1° to 50°.
17. The respiration therapy appliance of any one of the preceding items, wherein the axial bevel ranges from 1° to 25°.
18. The respiration therapy appliance of any one of the preceding items, wherein the axial bevel ranges from 2° to 20°.
19. The respiration therapy appliance of any one of the preceding items, wherein the axial bevel ranges of from 3° to 16°.
20. The respiration therapy appliance of any one of the preceding items, wherein the axial bevel ranges from 4° to 7°.
21. The respiration therapy appliance of any one of the preceding items, wherein the cutout is formed and arranged at the blade tip in such a way that the blade tip is curved or bent in an axial direction.
22. The respiration therapy appliance of any one of the preceding items, wherein the cutout is formed and arranged at the blade tip in such a way that the blade element has at least two different outer radii at the blade tip.
23. The respiration therapy appliance of any one of the preceding items, wherein a smaller outer radius of the blade element at the blade tip is arranged at or near the base of the blade element.
24. The respiration therapy appliance of any one of the preceding items, wherein a smaller outer radius of the blade element at the blade tip is arranged at or near a longitudinal side of the blade element.
25. The respiration therapy appliance of any one of the preceding items, wherein a smaller outer radius is arranged between the longitudinal side and the base of the blade element.
26. The respiration therapy appliance of any one of the preceding items, wherein the fan impeller is produced in one piece by injection molding.
27. The respiration therapy appliance of any one of the preceding items, wherein the cutouts have a smaller material thickness than the disk or the blade elements.
28. A fan impeller for a respiration therapy appliance, wherein the impeller comprises a plurality of blade elements which are arranged on a support disk, the blade elements and/or the support disk comprising at least one cutout.

LIST OF REFERENCE NUMERALS 1 respiration therapy appliance
2 fan
3 fan impeller
4 blade element
5 winglet
6 disk
13 side
14 longitudinal side
15 base
16 support disk
17 cutout/hole
18 circumference of support disk
19 outer radius of support disk
20 circumference of blade element
21 outer radius of blade element
22 blade tip
23 side
24 suction side
26 cover disk
32 rotation axis of fan impeller
33 hub
34 pressure side
100 operating device
101 display device
102 tube
103 control device
104 patient interface
200 pressure
201 volumetric flow
202 efficacy

What is claimed is:
1. A rotatable fan impeller for a respiration therapy appliance, wherein the impeller comprises a central hub with a single support disk which extends substantially in a radial direction starting from the hub, the single support disk having an outer radius which defines a circumference, a plurality of blade elements which are arranged with their base on the single support disk and starting from the hub extend substantially in a radial direction to their blade tip, and wherein a single through-hole is formed as cutout in the single support disk between at least some adjacent blade elements of the plurality of blade elements.

2. The fan impeller of claim 1, wherein the single through-hole is non-circular.

3. The fan impeller of claim 1, wherein the blade elements, starting from the hub, extend rectilinearly to their blade tip.

4. The fan impeller of claim 1, wherein the blade elements, starting from the hub, extend in a curved manner to their blade tip.

5. The fan impeller of claim 1, wherein also the blade elements comprise at least one cutout.

6. The fan impeller of claim 5, wherein the blade elements comprise a cutout which is arranged at the blade tip in such a way that the blade tip is beveled in an axial direction.

7. The fan impeller of claim 5, wherein the at least one cutout is formed and arranged at the blade tip in such a way that the blade tip is curved or bent in an axial direction.

8. The fan impeller of claim 5, wherein the at least one cutout is formed and arranged at the blade tip in such a way that the blade element has at least two different outer radii at the blade tip.

9. The fan impeller of claim 1, wherein a circumference of the blade elements is greater than a circumference of the single support disk.

10. A respiratory therapy appliance, wherein the appliance comprises at least one fan for generating a respiratory air flow for carrying out respiration therapy, the fan comprising the rotatable fan impeller of claim 1.

11. A rotatable fan impeller for a respiration therapy appliance, wherein the impeller comprises a central hub with a support disk which extends substantially in a radial direction starting from the hub, the support disk having an outer radius which defines a circumference, a plurality of blade elements which are arranged with their base on the support disk and starting from the hub extend substantially in a radial direction to their blade tip and starting from the base on the support disk extend in an axial direction and there define a longitudinal side, the blade elements having at least one outer radius at the blade tips, and wherein each blade element of the plurality of blade elements comprises a cutout which is arranged at the blade tip in such a way that the blade tip exhibits a single bevel in the axial direction, with an outer radius at the base of the blade element being smaller than an outer radius at the longitudinal side of the blade element, and wherein a single through-hole is formed as cutout in the support disk between at least some adjacent blade elements of the plurality of blade elements.

12. The fan impeller of claim 11, wherein a circumference of each blade element of the plurality of blade elements is greater than a circumference of the support disk.

13. The fan impeller of claim 11, wherein the axial bevel ranges from 1° to 50°.

14. The fan impeller of claim 11, wherein the axial bevel ranges from 4° to 7°.

15. The fan impeller of claim 11, wherein each blade element of the plurality of blade elements, starting from the hub, extends rectilinearly to its blade tip.

16. A respiratory therapy appliance, wherein the appliance comprises at least one fan for generating a respiratory air flow for carrying out respiration therapy, the fan comprising the rotatable fan impeller of claim 11.

17. The fan impeller of claim 11, wherein the blade elements, starting from the hub, extend in a curved manner to their blade tip.

18. A rotatable fan impeller for a respiration therapy appliance, wherein the impeller comprises a central hub with a single support disk which extends substantially in a radial direction starting from the hub, the single support disk having an outer radius which defines a circumference, a plurality of blade elements which are arranged with their base on the single support disk and starting from the hub extend substantially in a radial direction to their blade tip and starting from the base on the single support disk extend in an axial direction and there define a longitudinal side, the blade elements having at least one outer radius at the blade tips and, starting from the hub, extending rectilinearly to their blade tip, and wherein each blade element of the plurality of blade elements comprises a cutout which is arranged at the blade tip in such a way that the blade tip exhibits a single bevel in the axial direction, with an outer radius at the base of each blade element of the plurality of blade elements being smaller than an outer radius at the longitudinal side of the blade element, and wherein a single through-hole is formed as cutout in the single support disk between at least some adjacent blade elements of the plurality of blade elements.

19. The fan impeller of claim 18, wherein the blade elements, starting from the hub, extend rectilinearly to their blade tip.

20. The fan impeller of claim 18, wherein the blade elements, starting from the hub, extend in a curved manner to their blade tip.

* * * * *